(12) United States Patent
Mason

(10) Patent No.: US 8,076,526 B2
(45) Date of Patent: Dec. 13, 2011

(54) EXTRACTIVE DISTILLATION OF CONJUGATED DIENE

(75) Inventor: Robert W. Mason, Missouri City, TX (US)

(73) Assignee: Lyondell Chemical Technology, Houston, TX (US)

(*) Notice: Subject to any disclaimer, the term of this patent is extended or adjusted under 35 U.S.C. 154(b) by 450 days.

(21) Appl. No.: 12/383,904

(22) Filed: Mar. 30, 2009

(65) Prior Publication Data

US 2010/0243424 A1    Sep. 30, 2010

(51) Int. Cl.
*C07C 7/08* (2006.01)
(52) U.S. Cl. ......... 585/809; 585/833; 585/860; 585/865
(58) Field of Classification Search .......................... None
See application file for complete search history.

(56) References Cited

U.S. PATENT DOCUMENTS

| | | | |
|---|---|---|---|
| 4,277,315 A | 7/1981 | Volkamer et al. | |
| 4,555,312 A * | 11/1985 | Ogura et al. | 203/29 |
| 6,395,953 B1 | 5/2002 | Koga et al. | |
| 6,413,378 B1 * | 7/2002 | Kanauchi et al. | 203/1 |
| 7,348,466 B2 | 3/2008 | Bridges et al. | |
| 2002/0052533 A1 * | 5/2002 | Koga et al. | 585/313 |
| 2007/0055088 A1 * | 3/2007 | Schindler et al. | 585/702 |
| 2007/0256920 A1 * | 11/2007 | Kanauchi et al. | 203/2 |
| 2008/0183024 A1 * | 7/2008 | Klanner et al. | 585/633 |

* cited by examiner

*Primary Examiner* — Tam M Nguyen

(57) ABSTRACT

A process for isolating a conjugated diene from a hydrocarbon mixture is disclosed. The process comprises distilling the hydrocarbon mixture in the presence of an extraction solvent comprising an N,N-dialkyl aliphatic amide and from 12 to 50 weight percent furfural to separate a distillate and a conjugated diene-rich extract; and recovering the conjugated diene from the extract.

12 Claims, 2 Drawing Sheets

EXTRACTIVE DISTILLATION OF CONJUGATED DIENE

FIELD OF THE INVENTION

This invention relates to a process of isolating a conjugated diene from a hydrocarbon mixture.

BACKGROUND OF THE INVENTION

A conjugated diene such as 1,3-butadiene or isoprene is generally isolated and purified from a hydrocarbon mixture containing the conjugated diene, such as a $C_4$ hydrocarbon mixture or $C_5$ hydrocarbon mixture by a series of distilling operations, particularly extractive distillations. The problems of polymer formation can occur in extractive distillations, which can clog distillation equipments, for example, distillation columns, heat exchangers, reflux condensers, and evaporators. The polymer clogging problem causes frequent shutdowns of the operation so the polymer can be cleaned from the operating unit.

U.S. Pat. No. 6,395,953 teaches a process for preparing a purified conjugated diene by extractive distillation with an extraction solvent comprising an amide compound and 0.01 to 10 weight percent of a heterocyclic aldehyde. However, the polymer clogging problem still occurs during the distillation when such an extraction solvent is used. This invention is to reduce or prevent polymer clogging of distillation equipment during the extractive distillation of a conjugated diene from a hydrocarbon mixture.

SUMMARY OF THE INVENTION

Figure 1:
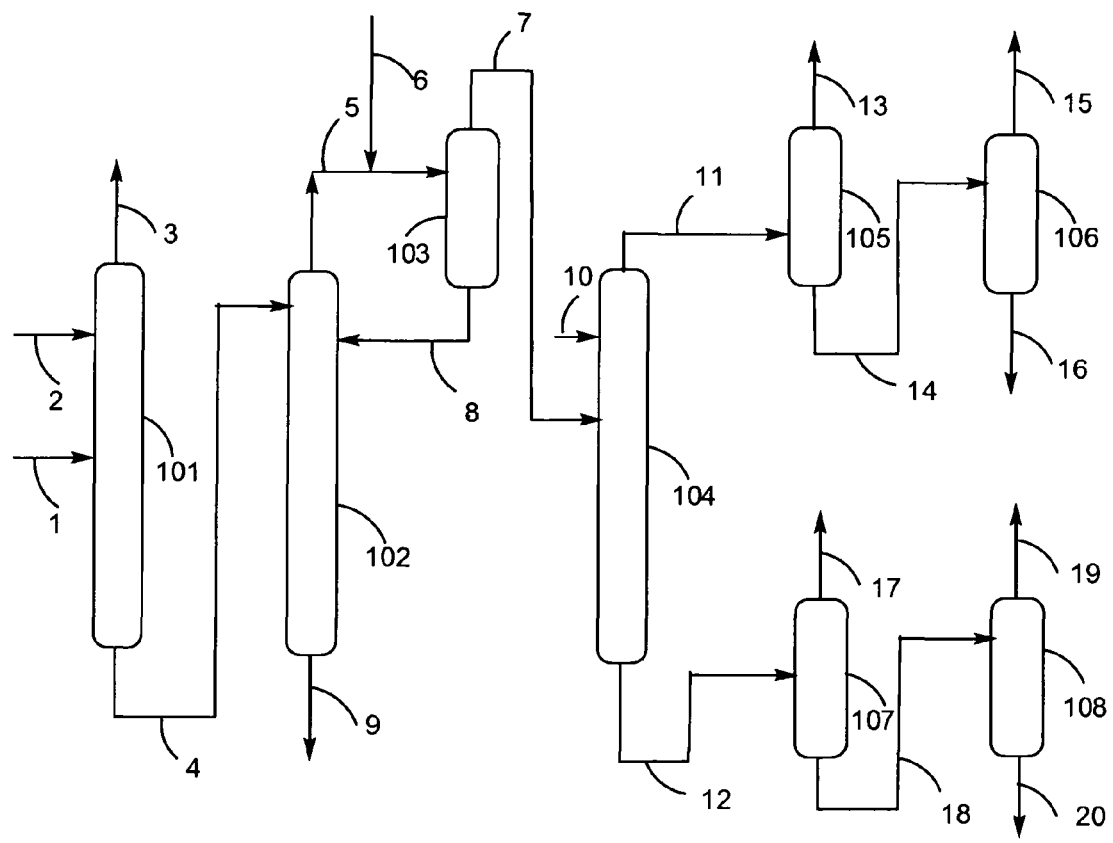
FIG. 1 is a schematic representation of one embodiment of the invention.

The invention is a process for isolating a conjugated diene from a hydrocarbon mixture. The process comprises (a) distilling the hydrocarbon mixture in the presence of an extraction solvent comprising an N,N-dialkyl aliphatic amide and from 12 to 50 weight percent furfural to separate a distillate from a conjugated diene-rich extract; and (b) recovering the conjugated diene from the extract.

DETAILED DESCRIPTION OF THE INVENTION

The process isolates a conjugated diene from a hydrocarbon mixture. The conjugated diene can be any $C_4$ or $C_5$ conjugated diene (containing 4 or 5 carbons). Preferably, the conjugated diene is 1,3-butadiene or isoprene. The source of the hydrocarbon mixture is not critical. The hydrocarbon mixture may be obtained by a thermal cracking process, a dehydrogenation of n-butane and/or n-butene, or a dehydrogenation of isopentane and/or isoamylene. An example of hydrocarbon mixtures is a $C_4$ hydrocarbon fraction containing 1,3-butadiene obtained from a steam cracking process. A $C_4$ hydrocarbon is a hydrocarbon molecule containing four carbon atoms. A $C_4$ hydrocarbon mixture such as naphtha-cracked petroleum generally contains propane, propylene, isobutene, allene, n-butane, isobutene, 1-butene, trans-2-butene, cis-2-butene, 1,3-butadiene, methylacetylene, 1,2-butadiene, and vinylacetylene. Another example of hydrocarbon mixtures suitable for the present invention is a $C_5$ hydrocarbon mixture containing isoprene obtained from a steam cracking process. The $C_5$ hydrocarbon mixture generally contains n-pentane, isopentane, 1-pentene, 2-methyl-1-butene, trans-2-pentene, cis-2-pentene, 2-methyl-2-butene, isoprene, trans-1,3-pentadiene, cis-1,3-pentadiene, 1,4-pentadiene, 2-butyne, isopropenyl-acetylene, isopropyl-acetylene, cyclopentane, cyclopentene, and cyclopentadiene. Such a hydrocarbon mixture is generally obtained by cracking naphtha and separating $C_2$ and $C_3$ hydrocarbons such as ethylene and propylene and heavier hydrocarbons such as those containing greater than six carbon atoms.

The process comprises an extractive distillation step. In an extractive distillation, an extraction solvent is used to increase the relative volatilities of the key components in the feed mixture. Alteration of the volatilities is desirable in systems having low relative volatilities or those which exhibit azeotropes. The extraction solvent will selectively interact with one or more components of the feed mixture thereby increasing relative volatilities. Purification of 1,3-butadiene and isoprene through extractive distillation are known (e.g., U.S. Pat. Nos. 6,395,953; 7,348,466; and 4,277,315).

The process uses an extraction solvent. The extraction solvent comprises an N,N-dialkyl aliphatic amide and from 12 to 50 weight percent (wt %) furfural. The term "extraction solvent" is used to refer to a single chemical compound (solvent) or a mixture of two or more compounds (solvents). Examples of suitable N,N-dialkyl aliphatic amides are dimethylformamide (DMF), diethylformamide, dimethylacetamide, diethylacetamide, and mixtures thereof. In general, N,N-dialkyl aliphatic amides boiling at from 150 to 260° C., preferably from 150 to 210° C. are used. It is particularly advantageous to use DMF. Preferably, the extraction solvent comprises 12 to 30 wt %, more preferably 15 to 25 wt % furfural. In such extraction solvent, the polymer formed from the conjugated diene has lower molecular weight than the polymer formed when the extraction solvent contains lower concentration of furfural (e.g., less than 10 wt %). Furthermore, the polymers formed are more soluble in the extraction solvent, thus it should reduce the polymer deposition on the interior of distillation columns, heat exchangers, condensers, evaporators, etc.

The amount of the extraction solvent relative to the hydrocarbon mixture is generally 1:1 to 10:1, preferably 2:1 to 8:1 by weight.

The process may use a single-stage or multi-stage, advantageously a two-stage, extractive distillation. For example, the conjugated diene is separated from the hydrocarbon mixture by subjecting the mixture, which contains both hydrocarbons which are more soluble and hydrocarbons which are less soluble than the conjugated diene, to an extractive distillation with the extraction solvent according to the invention, from which distillation a distillate containing the less soluble hydrocarbons and an extract containing the conjugated diene, the more soluble hydrocarbons, and the extraction solvent are obtained. The conjugated diene can be isolated, from the extract, in the form of a crude product which is of adequate purity for certain applications, but which may also be subjected to additional purification operations, for example, fractional distillation. Advantageously, however, the conjugated diene is isolated by using two successive extractive distillation stages using the extraction solvent. Generally, the conjugated diene isolated by the process has a purity of at least 95 wt %, more preferably at least 99 wt %.

When two-stage distillation is used, the first stage of the extractive distillation results in a first distillate comprising the less soluble hydrocarbons and a first extract comprising the conjugated diene, the more soluble hydrocarbons, and the extraction solvent. The first extract is further processed (e.g., by distillation) to give a mixture comprising the conjugated diene and the more soluble hydrocarbons. This mixture is subjected to a second extractive distillation using the extraction solvent, giving the conjugated diene as a second distillate, and a second extract which contains the more soluble hydrocarbons and the extraction solvent. The extraction solvent is removed from the second extract to give a stream comprising the more soluble hydrocarbons.

By way of example, the extractive distillation of a $C_4$ mixture in the presence of an extraction solvent containing DMF and furfural in a weight ratio of 80:20 gives a first distillate containing the butanes, butenes, and a first extract containing 1,3-butadiene, ethylacetylene, vinylacetylene, and 1,2-butadiene, DMF, and furfural. A mixture of 1,3-butadiene, ethylacetylene, vinylacetylene, and 1,2-butadiene is stripped from the first extract, and further subjected to a second stage extractive distillation with the extraction solvent (DMF and furfural), giving 1,3-butadiene as a second distillate and a second extract containing ethylacetylene, vinylacetylene, 1,2-butadiene, DMF, and furfural. The ethylacetylene, vinylacetylene and 1,2-butadiene are separated from the second extract in a stripping unit leaving a bottoms fraction containing DMF, furfural, and other heavier components. The bottoms fraction may be recycled to the extractive distillations or purified before it is recycled. The 1,3-butadiene obtained as the second distillate can subsequently be subjected to further fractional distillations to remove the very small amounts of $C_3$ and/or $C_5$ hydrocarbons which may still be present.

The extraction solvent may preferably contain an oxygen scavenger. Examples of the oxygen scavenger include nitrites such as calcium nitrite and sodium nitrite; amines such as hydroxylamine and hydrazine; dithionites such as sodium dithionite; and sulfites such as calcium sulfite, potassium sulfite, manganese sulfite and sodium sulfite. Among these, nitrites are preferred. Since oxygen in the extraction solvent is scavenged by the oxygen scavenger to inhibit radical formation, the polymerization-inhibiting effect is more enhanced. The concentration of the oxygen scavenger in the extraction solvent is generally 0.01 to 0.15 wt %, preferably 0.02 to 0.08 wt %.

The process may use a polymerization inhibitor. The polymerization inhibitors used in the present invention are generally capable of inhibiting or retarding the polymerization of a conjugated diene.

Examples of polymerization inhibitors which inhibit or retard polymerization by scavenging radicals with a stable radical include 1,1-diphenyl-2-picrylhydrazyl, 1,3,5-triphenylferudazyl, 2,6-di-t-butyl-α-(3,5-di-t-butyl-4-oxo-2,5-cyclohexadiene-1-indene)-p-tolyloxy, 2,2,6,6-tetramethyl-4-piperidone-1-oxy, 2,2,6,6-tetramethyl-4-hydroxyl-1-piperidinyloxy, N-(3-N-oxyanilino-1,3-dimethylbutylidene)-aniline oxide, and 2-(2-cyanopropyl)-ferudazyl.

Examples of polymerization inhibitors which inhibit or retard polymerization by a chain transfer reaction include compounds having an active NH bond, such as diphenylpicrylhydrazine, diphenylamine, diethylhydroxylamine, dimethylhydroxylamine, methylethylhydroxylamine, dipropylhydroxylamine, dibutylhydroxylamine and dipentylhydroxylamine; compounds having a phenolic OH bond, such as hydroquinone and t-butylcatechol; and dithiobenzoyl disulfide, p,p'-ditolyl trisulfide, p,p'-ditolyl tetrasulfide, dibenzyl tetrasulfide, and tetraethylthiuram disulfide.

Examples of polymerization inhibitors which inhibit or retard polymerization by an addition reaction include anthracene, 1,2-benzanthracene, tetracene, and chloranil; benzoquinone derivatives such as p-benzoquinone, 2,6-dichlorobenzoquinone, and 2,5-dichlorobenzoquinone; nitro compounds such as furfurylidenemalononitrile, trinitrobenzene, and m-dinitrobenzene; and nitroso compounds such as nitrosobenzene and 2-methyl-2-nitrosopropane.

FIG. 1 shows a butadiene extraction unit according to the invention. A crude $C_4$ feedstock 1 is fed to a first reboiled extractor 101. Feed 1 is typically first passed into a reboiled vaporizer drum (not shown), and then passed from that drum into extractor 101 at one or more points along the height of the extractor. Lean (essentially free of $C_4$ hydrocarbons) extraction solvent 2 is introduced into tower 101 above the point(s) of introduction of feed 1 so that the denser, descending extraction solvent can counter currently contact the feed which is rising inside tower 101. Extraction solvent 2 extracts butadiene and other more soluble components from feed 1 in known manner.

Extractor 101 has at its upper end a conventional reflux circuit that is not shown for sake of clarity but is like that of stripper 102. The first distillate 3 (butanes, butenes, etc.) is removed from this circuit for further processing elsewhere. Tower 101 has a conventional reboiler loop (not shown) for heating the tower.

Bottoms stream 4 (first extract) from tower 101 is a mixture of mostly butadiene and extraction solvent and are passed to first reboiled stripper 102 to separate butadiene and other hydrocarbons from the solvent. Bottoms stream 9 from tower 102 is primarily extraction solvent and heavy materials, of which at least part is removed for reclamation and reuse in the extraction unit as lean extraction solvent.

Primarily butadiene, after separation from the extraction solvent, is recovered as overhead from tower 102 in line 5 and enters a conventional reflux circuit composed of at least one heat exchanger (not shown) and reflux drum 103. Liquid reflux is returned to tower 102 by way of line 8, while a vapor stream rich in butadiene is recovered in line 7 for transport to a compression operation (not shown) before it is fed to a second reboiled butadiene extractor 104. Lean extraction solvent 10 is introduced into tower 104 near the top of the tower so that, when descending through tower 104 in the same manner described for tower 101, it counter-currently contacts ascending feed from line 7. The second reboiled butadiene extractor 104 is equipped with an heat exchanger and a reflux drum (not shown). An overhead stream (second distillate) from extractor 104 is fed via line 11 to a first reboiled fractionator 105. In distillation column 105, stream 11 is distilled and materials lighter than butadiene are removed overhead by line 13 through a conventional reflux circuit (not shown) for ultimate removal from the extraction unit for use elsewhere in the plant, e.g., as fuel. The bottoms of tower 105 are removed by way of line 14 and introduced into a reboiled fractionator 106 wherein materials heavier than butadiene are removed as bottoms by way of line 16 for use elsewhere in the plant, e.g., as fuel. The overhead 15 from tower 106 passes through a conventional reflux circuit (not shown) and is then removed as the butadiene product.

Bottoms stream 12 (second extract) of tower 104 contains primarily solvent, heavy materials, and slight amounts of butadiene and $C_3$ and $C_4$ acetylenes, and is passed to a reboiled butadiene recovery column 107. Column 107 typically does not have a reflux circuit for its overhead 17. Overhead 17 is returned directly to line 6 of first stripper 102. Bottoms stream 18 of column 107 is primarily mixed extraction solvents, heavy materials, and acetylenes, and is passed to a second reboiled stripper 108 wherein light materials are stripped from the extraction solvent and heavies, and recovered overhead for use elsewhere in the plant, e.g., as fuel. Tower 108 typically has a reflux circuit (not shown). Bottoms stream 20 of tower 108 contains primarily the extraction solvent and heavies, and is recovered for reuse in the butadiene extraction process or is sent to the solvent reclamation unit.

Example 1

Polymerization of Isoprene

Isoprene (from Aldrich) is distilled to remove t-butyl catechol inhibitor. A solution containing distilled isoprene (9.06 g) and a solvent mixture (DMF to furfural is 80 to 20 by weight, 9.06 g) is sealed in a 50-mL Parr reactor. The reactor is pressurized with 200 psig nitrogen, vented to 1 atmosphere, then pressurized again with 200 psig nitrogen. The oxygen content in the head space is estimated to be about 940 ppm. The reactor is heated to 120° C. (248 F) and the reaction lasted for 22 h under stirring at 120° C. After being cooled, the reactor content is diluted to 50 mL with tetrahydrofuran and the polymer content analyzed by gel permeation chromatography (Agilent mixed CPLGel column, THF elution), externally calibrated with various commercially available polybutadiene and polyisoprene molecular weight standards. Isoprene conversion to polymer is 3.9%, with an average polymer molecular weight of 96,280.

Figure 2:
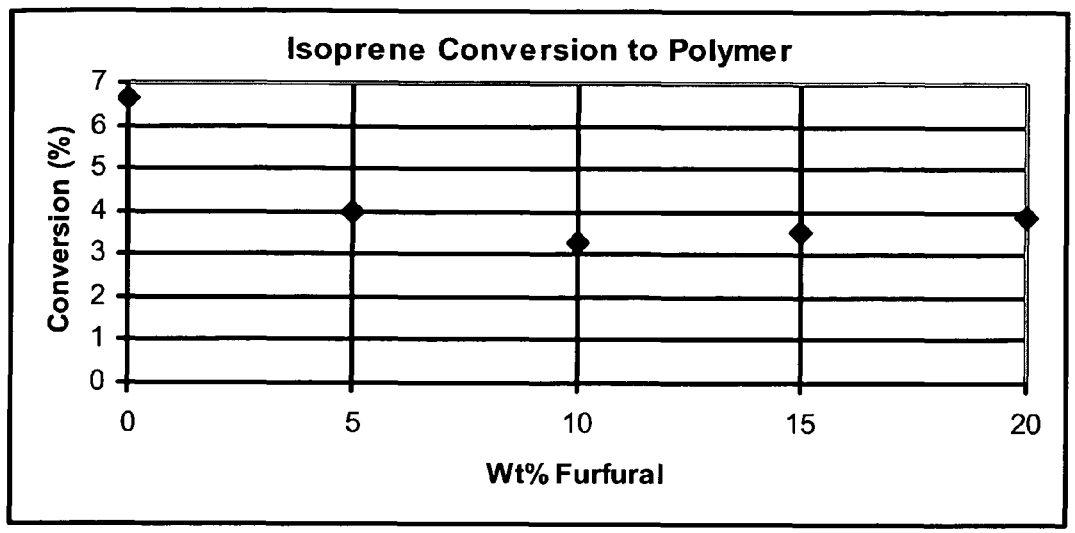
FIG. 2 is a graph showing the effect of the composition of the solvent on the isoprene conversion to the polymer at 120° C.
Figure 3:
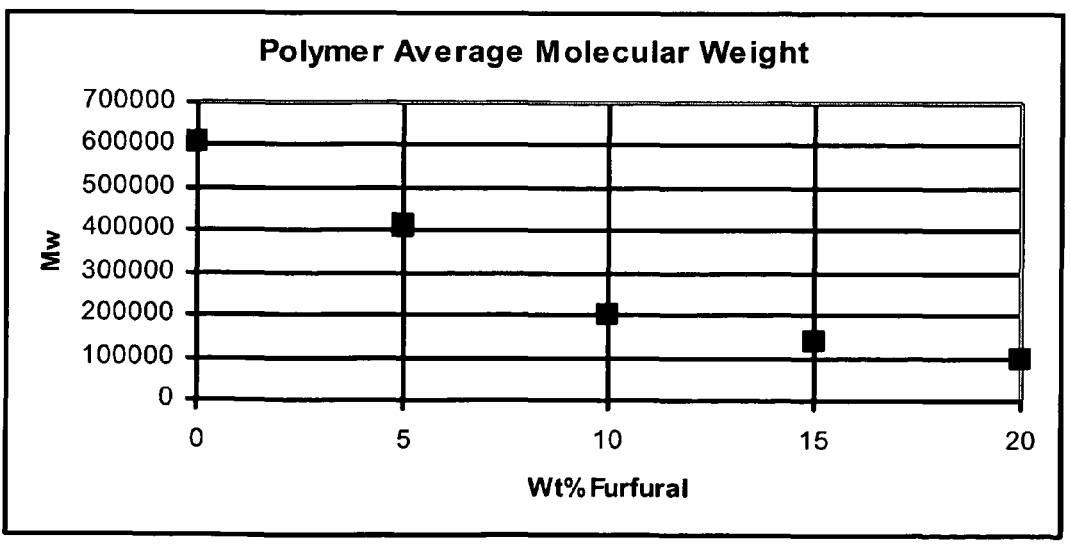
FIG. 3 is a graph showing the effect of the composition of the solvent on the average molecular weight of the polymer formed at 120° C.

The above procedure is repeated with other solvent mixtures. The results are shown in Table 1 and FIGS. 2 and 3. Results show that the amount of polymer formed is the lowest when the solvent contains about 10 wt % furfural. However, as the concentration of the furfural increases, the molecular weight of the polymers formed decreases. In addition, the polymers with lower molecular weights are more soluble in the mixed solvent.

TABLE 1

| Test | Wt % Furfural | Conversion (%) | Mw |
| --- | --- | --- | --- |
| 1 | 0 | 6.63 | 607,000 |
| 2 | 5 | 3.98 | 406,000 |
| 3 | 10 | 3.29 | 200,800 |
| 4 | 15 | 3.52 | 139,880 |
| 5 | 20 | 3.90 | 96,280 |

Example 2

Extractive Distillation

An extraction unit as depicted in FIG. 1 is operated using a crude $C_4$ feedstock 1 for extractor 101 that contains about 6.8 wt % n-butane, about 1.3 wt % isobutane, about 13.5 wt % 1-butene, about 10.3 wt % 2-butenes (cis and trans), about 27.9 wt % isobutylene, about 39.5 wt % butadienes (1,2- and 1,3-), about 0.5 wt % vinyl acetylene, and about 0.1 wt % ethyl acetylene, all wt % being based on the total weight of the feed. Feed 1 is introduced into extractor 101 at a temperature of about 125 F at about 65 psig, and a flow rate of about 60,000 pounds per hour (pph).

The extraction employs a mixture of DMF and furfural (weight 80:20) as the extraction solvent. The extraction solvent enters the extractor 101 via line 2 at a temperature of about 104 F at about 48 psig, and a flow rate of about 415,000 pph.

Extractor 1 is operated with a bottom temperature of about 260 F at 80 psig, and an overhead temperature of about 110 F at about 50 psig with an external reflux rate of about 45,000 pph. Extractor 101 produces about 35,000 pph of raffinate ($C_4$ hydrocarbons essentially free of 1,3-butadiene) in line 3 at about 110 F. Butadiene-rich solvent (mostly 1,3-butadiene, DMF, and furfural) is removed as bottoms 4 at a flow rate of about 351,000 pph and passed to first stripper 102.

Stripper 102 has a bottom temperature of about 335 F at about 6 psig, and a reflux rate of about 45 gallons per minute (gpm). About 60,000 pph of butadiene rich gas is removed from reflux drum 103 via line 7 and passed to a compression unit (not shown). About 30,000 pph of compressed gas is fed to second extractor 104. Bottoms stream 9 (mostly DMF, furfural, and other heavy components) of stripper 102 is at about 335 F at 6 psig. Bottoms stream 9 is sent to a solvent reclamation unit.

Lean extraction solvent 10 (mostly DMF and furfural) is introduced into tower 104 near the top of the tower so that, when descending through tower 104 in the same manner described for tower 101, it counter-currently contacts ascending feed from line 7. Extractor 104 is operated at a bottom temperature of about 258 F at about 48 psig, a top temperature of about 110 F at 50 psig, and a reflux rate of about 30,000 pph. Bottoms stream 12 (mostly DMF, furfural, and other heavy components) of extractor 104 is removed at a rate of about 50,000 pph and sent to butadiene removal column 107.

Column 107 is operated at a bottom temperature of about 260 F at about 5 psig. Overhead 17 (mostly recovered 1,3-butadiene), at about 210 F and 5 psig, is sent to first stripper 102 via line 6 at a flow rate of about 3,000 pph. Bottoms stream 18 (primarily DMF, furfural, and some 1,3-butadiene, ethyl- and vinyl-acetylenes), at a flow rate of about 47,000 pph, is sent to second stripper 108.

Second stripper 108 is operated at a bottom temperature of about 325 F at 3.5 psig using a reflux rate of about 12 gpm. Bottoms stream 20 (lean solvent) is sent to a solvent reclamation unit at the flow rate of about 45,000 pph. Overhead 19 (containing 1,3-butadiene, ethyl- and vinyl-acetylenes, 1,2-butadiene) is removed from the extraction unit.

Overhead 11 of extractor 104 is sent by way of line 11 to first fractionator 105 at the rate of about 27,000 pph. Tower 105 is operated with a bottom temperature of about 116 F at about 53 psig overhead. Light components are collected from line 13 (mostly 1,3-butadiene and methyl acetylene) and are used as fuel. Bottoms stream 14 (1,3-butadiene and small amounts of cis- and trans-2-butenes) is passed to second fractionator 106 for final separation of 1,3-butadiene product from the remaining solvent. Tower 106 is operated at a bottom temperature of about 140 F at 70 psig, with a reflux rate of about 180,000 pph. Final butadiene product is removed by way of overhead stream 15 (1,3-butadiene product) at the rate of about 26,000 pph. Bottoms stream 16 (mostly cis-2-butene and 1,2-butadiene and small amount of 1,3-butadiene) and is removed from the extraction process and is used as fuel.

I claim:
1. A process for isolating a conjugated diene from a hydrocarbon mixture, comprising (a) distilling the hydrocarbon mixture in the presence of an extraction solvent comprising an N,N-dialkyl aliphatic amide and from 12 to 50 weight percent furfural to separate a distillate and a conjugated diene-rich extract; (b) recovering the conjugated diene from the extract.

2. The process of claim 1 wherein the extraction solvent comprises 12 to 30 percent by weight of furfural.

3. The process of claim 1 wherein the extraction solvent comprises 15 to 25 percent by weight of furfural.

4. The process of claim 1 wherein the N,N-dialkyl aliphatic amide is selected from the group consisting of dimethylformamide, diethylformamide, dimethylacetamide, diethylacetamide, and mixtures thereof.

5. The process of claim 1 wherein the N,N-dialkyl aliphatic amide is dimethyl formamide.

6. The process of claim 1 wherein the conjugated diene is 1,3-butadiene.

7. The process of claim 1 wherein the conjugated diene is isoprene.

8. The process of claim 1 wherein the extractive distillation is a two-stage distillation.

9. The process of claim 1 further comprising separating the extract into a diene fraction and a recovered solvent and recycling at least a portion of the recovered solvent to the extractive distillation.

10. The process of claim 9 wherein the recovered solvent is purified before it is recycled to the extractive distillation.

11. The process of claim 1 employing an oxygen scavenger.

12. The process of claim 1 employing a polymerization inhibitor.

* * * * *